(12) United States Patent
Juvonen et al.

(10) Patent No.: US 8,530,500 B2
(45) Date of Patent: Sep. 10, 2013

(54) STABLE PHARMACEUTICAL OMEPRAZOLE FORMULATION FOR ORAL ADMINISTRATION

(75) Inventors: Erik Juvonen, Avondale, PA (US); Louis Massimo Micolucci, Cochranville, PA (US)

(73) Assignee: Vetegen, LLC, Kennett Square, PA (US)

( * ) Notice: Subject to any disclaimer, the term of this patent is extended or adjusted under 35 U.S.C. 154(b) by 36 days.

(21) Appl. No.: 12/839,495

(22) Filed: Jul. 20, 2010

(65) Prior Publication Data

US 2011/0015233 A1    Jan. 20, 2011

Related U.S. Application Data

(60) Provisional application No. 61/226,890, filed on Jul. 20, 2009.

(51) Int. Cl.
*A61K 31/4439* (2006.01)
*A61P 1/04* (2006.01)

(52) U.S. Cl.
USPC .......................................... 514/338; 424/400

(58) Field of Classification Search
None
See application file for complete search history.

(56) References Cited

U.S. PATENT DOCUMENTS

| 6,316,481 | B1 * | 11/2001 | Freehauf | 514/393 |
| 2003/0215496 | A1 | 11/2003 | Patel et al. | |
| 2005/0054682 | A1 * | 3/2005 | Phillips | 514/338 |
| 2005/0112193 | A1 | 5/2005 | Phillips et al. | |
| 2005/0239845 | A1 | 10/2005 | Proehl et al. | |
| 2009/0123390 | A1 * | 5/2009 | Hill | 424/45 |

FOREIGN PATENT DOCUMENTS

| WO | 0050038 | 8/2000 |
| WO | 0151050 | 7/2001 |

OTHER PUBLICATIONS

International Search Report mailed Mar. 29, 2011 in related PCT Application No. PCT/US2010/042508.
Supplementary European Search Report dated Nov. 28, 2012 in related EP Patent Application No. EP 10802745.

* cited by examiner

*Primary Examiner* — Robert A Wax
*Assistant Examiner* — Danah Al-Awadi
(74) *Attorney, Agent, or Firm* — Scully, Scott, Murphy & Presser, P.C.

(57) ABSTRACT

The present invention is directed to a pharmaceutical solution or syrup formulation for oral administration comprising; omeprazole, a solubilizing agent, a sweetening agent, a flavoring agent, and an antioxidant.

52 Claims, 5 Drawing Sheets

FIGURE 1

| Weight (g) | | | | | | |
|---|---|---|---|---|---|---|
| Composition | Formula 1 | Formula 2 | Formula 3 | Formula 4 | Formula 5 | Formula 6 |
| Omeprazole Sodium | 12.15 | 12.15 | 12.15 | 12.15 | 12.15 | 12.15 |
| Polyethylene Glycol 200 | \ | \ | 37.85 | \ | \ | \ |
| Polyethylene Glycol 300 | 37.85 | 28.85 | \ | 18.9 | 15.0 | 34.35 |
| Propylene Glycol | \ | 9.0 | \ | 18.9 | 15.0 | \ |
| Sorbitol | \ | \ | \ | \ | 7.85 | \ |
| Sodium Phosphate | \ | \ | \ | \ | \ | 1.0 |
| Water | \ | \ | \ | \ | \ | 2.5 |
| Total Weight | 50 | 50 | 50 | 50 | 50 | 50 |

FIGURE 2

| Formulation | Viscosity Time=0 weeks (cPs) | Viscosity Time=2 weeks (cPs) | Viscosity Time=4 weeks (cPs) |
|---|---|---|---|
| Formula 1 | 878 | 748 | 756 |
| Formula 2 | 580 | 448 | 495 |
| Formula 3 | 511 | 480 | 448 |
| Formula 4 | 409 | 370 | 354 |
| Formula 5 | 880 | 715 | 676 |
| Formula 6 | 630 | 354 | 401 |

FIGURE 3

| Formulation | Assay Time=0 weeks | Assay Time=4 weeks |
|---|---|---|
| Formula 1 | 105.1 | 107.3 |
| Formula 2 | 105.2 | 107.2 |
| Formula 3 | 105.1 | 110.6 |
| Formula 4 | 99.3 | 104.4 |
| Formula 5 | 103.8 | 104.3 |
| Formula 6 | 109.5 | 110.7 |

FIGURE 4

| Formulation | Time=0 weeks | | Time=2 weeks | | Time=4 weeks | |
|---|---|---|---|---|---|---|
| | Assay | LSI (%) | Assay | LSI (%) | Assay | LSI (%) |
| Formula 1 | 105.1 | ND | 107.5 | 0.13 | 104.2 | 0.24 |
| Formula 2 | 105.2 | ND | 110 | 0.34 | 98.9 | 0.65 |
| Formula 3 | 105.1 | ND | 104.4 | 0.27 | 99.8 | 0.52 |
| Formula 4 | 99.3 | ND | 109.4 | 0.55 | 98.2 | 1.1 |
| Formula 5 | 103.8 | ND | 106.9 | 0.62 | 96.5 | 1.2 |
| Formula 6 | 109.5 | ND | 111.1 | 0.39 | 98.8 | 0.83 |

ND=Not Detectable
LSI=Largest Single Impurity

FIGURE 5

STABLE PHARMACEUTICAL OMEPRAZOLE FORMULATION FOR ORAL ADMINISTRATION

CROSS REFERENCE TO RELATED APPLICATIONS

This application claims the benefit of U.S. Provisional Application No. 61/226,890 filed on Jul. 20, 2009, the entire contents of which are incorporated herein by reference.

BACKGROUND OF THE INVENTION

Omeprazole is a proton pump inhibitor that regulates the final step in hydrogen ion production and blocks gastric acid secretion in the gastrointestinal tracts of mammals. Omeprazole is used in mammals to treat peptic ulcers, dyspepsia and gastroesophageal reflux disease among other conditions. Omeprazole is effective because it acts to provide a long lasting reduction of gastric acid production.

Proton pump inhibitors, such as omeprazole, act by irreversibly blocking the hydrogen/potassium adenosine triphosphatase enzyme system ($H^+/K^+$ ATPase) of the gastric parietal cell. The proton pump is the terminal stage in gastric acid secretion and is directly responsible for secreting $H^+$ ions into the lumen of the stomach. The lack of acid in the stomach lumen aids in the healing of duodenal ulcers, reduces the pain from indigestion and reduces the frequency and severity of heartburn.

Currently, omeprazole for oral administration is provided in paste form for veterinary use. This paste is a thick consistency which does not flow without an applied pressure, similar to a thick toothpaste. The prior art teaches a 37% omeprazole in paste form with a typical dosage unit containing approximately 2.28 grams omeprazole. The prior art paste provides about a 10.5% bio-availability. The prior art paste also contains a hydrophobic oily liquid vehicle as an inert filler aiding the isolation of the omeprazole from moisture. This hydrophobic oily liquid is used as a carrier for dispersing the active omeprazole in the formulation before the addition of a thickening agent. The prescribed oral dose of the product is 4 mg/kg, once daily for four weeks. The solubility of omeprazole is 0.5 mg/mL in water, >19 mg/mL in dimethyl sulfoxide (DMSO), 20 mg/mL in Polyethylene Glycol 400 and 4.5 mg/mL in ethanol. Omeprazole is not very stable in water, ethanol or in acidic environments. Omeprazole decomposes rapidly at pH levels below about 4, with a half-life at neutral pH of about 14 hours. Omeprazole is very stable at pH levels above 7 if it protected from light and extremes in temperature and humidity. The drug is delivered in a paste or solid dose form in the prior art because of the instability of omeprazole in the presence of moisture.

What is desired is an oral solution or syrup formulation of omeprazole as a single or multi-dose application for use in the veterinary field.

SUMMARY OF THE INVENTION

The present invention is directed to a palatable pharmaceutical solution or syrup formulation for oral administration comprising; omeprazole, a solubilizing agent, a basifying agent, a sweetening agent, a flavoring agent, and an antioxidant.

The present invention is also directed to a palatable pharmaceutical solution or syrup formulation for oral administration comprising; an omeprazole salt, a solubilizing agent, a sweetening agent, a flavoring agent, a buffer, and an antioxidant.

BRIEF DESCRIPTION OF THE DRAWINGS

The present invention will be better understood by reference to the following drawings of which.

DETAILED DESCRIPTION OF THE INVENTION

The present invention provides a first embodiment of a pharmaceutical solution or syrup formulation for oral administration comprising: omeprazole; a solubilizing agent, a basifying agent, a sweetening agent, a flavoring agent, and an antioxidant which can be readily administered to animals, and preferably horses. By "syrup" is meant a formulation that has a flow characteristic of thick, artificial maple syrup; will flow without applied pressures, does not deposit any solids and is sticky or tacky to the touch. Another meaning of the term "syrup" is a viscous concentrated solution of a sugar, such as sucrose, in water or other aqueous liquid; combined with other ingredients, such a solution is used as a flavored vehicle for medications, as stated in Saunders Comprehensive Veterinary Dictionary, 3 ed. ©2007 Elsevier, Inc. The syrup formulation in accordance with the invention is not a paste as pastes are commonly understood in the art. The syrup of the present invention has a viscosity of between about 100 and 3500 centipoise at about 2.5 rpm to about 30 rpm as determined by a Brookfield Viscometer, using a cone and plate attachment, at about 22° C. In a further embodiment, the syrup of the present invention has a viscosity of between about 350 and about 1000 centipoise. In a further embodiment the syrup formulation of the present invention has the consistency of clear honey. The first pharmaceutical solution or syrup formulation in accordance with the present invention can contain a single basifying agent in a predetermined amount.

The present invention also provides a second embodiment of a pharmaceutical solution or syrup formulation for oral administration comprising: an omeprazole salt; a solubilizing agent, a sweetening agent, a flavoring agent, a buffer, and an antioxidant which can be readily administered to animals, and preferably horses. The second formulation comprises an omeprazole salt but does not comprise a basifying agent. The omeprazole salt can comprise alkali metal salts including sodium, lithium and potassium salts, among others. The omeprazole salt can also comprise alkaline earth and transition metal salts, such as calcium and magnesium salts, among others.

The present invention also provides a third embodiment of a pharmaceutical solution or syrup formulation for oral administration comprising: omeprazole; a solubilizing agent, two or more basifying agents, a sweetening agent, a flavoring agent, and an antioxidant which can be readily administered to animals, and preferably horses.

The above embodiments comprise the proton pump inhibitor omeprazole. Other proton pump inhibitors may also be used, singularly or in combination with each other or omeprazole. As an example, other proton pump inhibitors may include benzimidazole derivatives, including, but not limited to, lansoprazole, dexlansoprazole, esomeprazole, timoprazole, picoprazole, pantoprazole, rabeprazole, thiadiazole and thiazole and imidazopyridine derivatives. The proton pump inhibitor provides a pronounced and lasting reduction of gastric acid production. Other proton pump inhibitors and other compounds could also be used which block the hydrogen/potassium adenosine triphosphatase enzyme system (the $H^+/K^+$ ATPase) of the gastric parietal cell.

Omeprazole or other proton pump inhibitors can optionally be covered with a coating before being introduced with the other elements in the composition. Prior to preparation of the composition, the raw omeprazole or other proton pump inhibitor material can be obtained in granule form. In one example, each granule of omeprazole or other proton pump inhibitors can be covered with a coating, such as, for example, an enteric coating which would degrade when in contact with an acidic medium. In another example, several granules of omeprazole or another proton pump inhibitor can be covered with a coating. Other coatings may include, for example, polyvinylpyrrolidone, microcrystalline cellulose, hydroxypropyl methylcellulose, hydroxypropyl cellulose, polymers, latex polymers, an acrylic polymer, cellulose acetate phthalate, cellulose acetate trimellitate, diethylphthalate, ethylcellulose, hydroxypropyl cellulose, hydroxypropyl methylcellulose phthalate, methylcellulose, polyethylene glycol, polyvinyl alcohol, polyvinyl pyrrolidone, polyvinyl acetate phthalate, triethylcitrate, polysorbate and povidone.

The enteric coating may be any coating that protects the granules from gastric contents, for example a coating that is stable at acidic pH, but can break down rapidly at higher pH or a coating whose rate of hydration or erosion is slow enough to ensure that contact of gastric contents with the digestive enzymes is reduced as compared to an un-coated granule while it is in the stomach, as opposed to the remainder of the gastro-intestinal tract. The enteric coating or coatings are applied onto the granule or granules by using a suitable coating technique. The enteric coating layer material may be dispersed or dissolved in either water or in suitable organic solvents. The following non-limiting examples may be used as an enteric coating: such as modified or unmodified natural polymers such as cellulose acetate phthalate, hydroxypropylmethylcellulose phthalate, hydroxypropylmethylcellulose acetate succinate, and shellac; or synthetic polymers such as acrylic polymers or copolymers methacrylic acid polymers and copolymers, methylmethacrylate copolymers, and methacrylic acid/methylmethacrylate copolymers.

The enteric coating can also be a synthetic polymer and optionally include an inorganic material such as an alkalinizing agent. The resulting coated granules provide a delayed release of the omeprazole or other proton pump inhibitor to the gastro-intestinal tract. The enteric coating layers may contain one or more pharmaceutically acceptable plasticizers to obtain the desired mechanical properties, such as flexibility and hardness of the enteric coating layers. Such plasticizers are for instance, but not limited to, triacetin, citric acid esters, phthalic acid esters, dibutyl sebacate, cetyl alcohol, polyethylene glycols, polysorbates or other plasticizers.

The individually coated granules can also be compressed to form a grouping of granules. This compression can occur prior to coating, so that the compressed mass of granules would be coated all together. The compression can also occur after coating, forming a compressed mass of individually coated granules. The amount of plasticizer can be optimized for each enteric coating layer formula, in relation to selected enteric coating layer polymers, selected plasticizers and the applied amount of the polymers in such a way that the mechanical properties are adjusted so that the acid resistance of the group of granules does not decrease significantly during compression of granules into groups of granules. To protect the granules or groups of granules from an acidic environment, the enteric coating layer or layers is added until a thickness of about 20 μm. The maximum thickness of the applied enteric coating layer or layers is determined by the specific processing conditions.

The individual granules or mass of granules can then be introduced to the other elements which form the compositions and formulations of the present invention. All embodiments of the present application may include coated granules, coated masses of granules or un-coated granules. All embodiments of the present application can comprise the omeprazole in solution or in suspension. When the omeprazole is held in solution, the granules or mass of granules are of sufficient size to be solubilized within a reasonable time. When the omeprazole is held in suspension, the granules or mass of granules are of sufficient size to remain in suspension.

The granules can have any suitable size or shape. The term "granule" or "granules" as used herein includes fine powders having particle diameters in the range of about 50 μm-5,000 μm.

The pharmaceutical solution or syrup formulation embodiments have a syrupy consistency, similar to artificial maple syrup, with many of the same characteristics. These embodiments flow without applied pressures, do not deposit any solids and are sticky or tacky to the touch. These formulation embodiments do not contain a hydrophobic oily liquid vehicle.

The particular amount of omeprazole in any of the present embodiments is not critical, but typically comprises between about 200 mg/mL to about 500 mg/mL (w/v). The omeprazole or omeprazole sodium salt is typically in powder form prior to addition of the other constituents of the embodiments. The embodiments are designed for single or multi-dose applications.

Suitable solubilizing agents for use in the present embodiments are, for example, dimethylisosorbide, polyethylene glycol 200 (PEG 200), polyethylene glycol 300 (PEG 300), polyethylene glycol 400 (PEG 400), propylene glycol, glycerol, sorbitol and combinations thereof. The preferred solubilizing agents are PEG 300 and propylene glycol.

Suitable basifying agents for use in the first and third embodiments are, for example, organic amines, monoethanolamine, diethanolamine, sodium phosphate, and inorganic bases, for example, anhydrous potassium hydroxide and combinations thereof. A basifying agent is employed in a first embodiment, with no basifying agents being used in the second embodiment. Two or more basifying agents are employed in a third embodiment. The third embodiment contains a combination of two or more basifying agents, with the total amount of the combination of two or more basifying agents being the same or different than the basifying agent in the first embodiment. The basifying agents may be selected from the following non-exhaustive list including monoethanolamine, diethanolamine, triethylamine, organic amines, monoethanolamine, diethanolamine, sodium phosphate, and inorganic bases, for example, anhydrous potassium hydroxide and combinations thereof. The preferred basifying agent is monoethanolamine. To achieve a sufficient environment for the omeprazole to act, the basifying agent serves two functions. The basifying agent's first function is to de-protonate one nitrogen, consequently converting omeprazole to R-ammonium salt. The second function of the basifying agent is to keep gastric environment less acidic, so as to stabilize omeprazole in vivo.

Suitable sweetening agents for use in any of the present embodiments are, for example, stevia, sucralose, saccharin and aspartame. These four examples in no way limit the choices for the addition of sweetening agents, which can be any of many agents known in the art which are palatable for a specific animal.

Suitable flavoring agents for use in any of the present embodiments are, for example, apple and rosemary. These two examples in no way limit the choices for the addition of flavoring agents, which can be any of many agents known in the art which are palatable for a specific animal.

Suitable antioxidants for use in any of the present embodiments are, for example, butylated hydroxyanisole (BHA), butylated hydroxytoluene (BHT), and propyl gallate. The preferred antioxidant is BHT.

Any of the present embodiments may include additional ingredients used in veterinary medicines. For example, antimicrobial agents such as benzoic acid or sodium benzoate; solubility enhancers such as cyclodextrins, Polyoxyethylene (20) sorbitan monooleate (Polysorbate 80) and Soluble polyvinyl pyrrolidone (Kollidon 17) and viscosity modifiers such as hydroxyproxymethyl cellulose, hydroxypropyl methylcellulose (HPMC) and xantham gum may be added.

Either the first, second or third embodiments of a pharmaceutical solution or syrup formulation may also be concentrated. A concentrated solution or syrup formulation of any of the embodiments may be included in a kit. This concentrated solution may be diluted with a dilutant to a predetermined concentration. This kit may comprise an amount of a concentrated solution or syrup formulation, a vessel which is sufficiently sized to hold a mixture of the concentrated solution or syrup formulation and the dilutant, and a syringe for injecting the mixture into an animal's mouth. The dilutant may be any pharmaceutically acceptable dilutant, preferably water.

The embodiments of these formulations may be administered to treat peptic ulcers, dyspepsia and gastroesophageal reflux disease, among other conditions. The embodiments of these formulations are preferably used in the veterinary field for mammals including, but not limited to cattle, pigs and horses. The embodiments of these formulations are preferably prepared for horses. However, the embodiments of these formulations may also be administered to humans. The embodiments of these formulations can be administered or delivered into the interior of an animal's mouth, which subsequently swallows the formulation. This method of treatment, comprising a solution or syrup, is especially useful for humans and animals that have difficulty swallowing because of disease or age. The embodiments of these formulations, depending on the particular animal and its needs, may include a single dose of omeprazole or several doses over time. "Several doses" means two or more doses delivered sequentially over a 24 hour period such as two times a day, 12 hours apart or two times per day, 4, 6, or 8 hours apart. By "single dose" is meant one bolus dose clinically administered at one time without need for daily or subsequent administrations.

The amount of the formulation of each embodiment to be administered may vary according to the particular animal species to be treated, the severity of the disease, the physical condition of the animal, and other pertinent factors. A veterinarian or one skilled in the art of animal treatment can determine the particular dosage amount for an animal based on the animal's characteristics and condition. Usually, based on the veterinarian or one skilled in the art's experience, a dosage of omeprazole of about 0.2 mg/kg to about 20 mg/kg is used.

The following examples of the embodiments of the present formulations are provided herein. Examples 1-4 represent exemplary formulations of the first embodiments. Examples 5-8 represent exemplary formulations of the second embodiment. Examples 5-8 do not include a basifying agent because the embodiment comprises a salt. Examples 5-8 also comprise a buffer so that the omeprazole is protected in a buffered environment from the acid levels in the gastric system, in vivo. For each of the examples, 2 mg of sodium benzoate may be added to either the first or second formulation prior to the addition of a sufficient quantity of glycerol or sorbitol. For each of the examples, 0.2 mg of a viscosity modifier can be added depending on the desired viscosity of the formulation.

Example 1

500 mg of omeprazole is added to 5 mL PEG 300 or 5 mL of propylene glycol. The mixture is stirred and 0.2 mL monoethanolamine base was added. 2 mg of BHT, 10 mg of a sweetening agent and 10 mg of a flavoring agent are added to the mixture followed by the addition of a sufficient quantity of glycerol to bring the entire mixture to a volume of 10 mL. The amounts of the sweetening agent and flavoring agent can be adjusted to taste, in order to make a more palatable formulation. Various combinations of glycerol and PEG 300 can also be used to get the formulation to the desired consistency.

Example 2

500 mg of omeprazole is added to 5 mL PEG 300 or 5 mL of propylene glycol. The mixture is stirred and 0.2 mL monoethanolamine base is added. 2 mg of BHT, 10 mg of a sweetening agent and 10 mg of a flavoring agent are added to the mixture followed by the addition of a sufficient quantity of sorbitol to bring the entire mixture to a volume of 10 mL. The amounts of the sweetening agent and flavoring agent can be adjusted to taste, in order to make a more palatable formulation. Various combinations of sorbitol and PEG 300 can also be used to get the formulation to the desired consistency.

Example 3

500 mg of omeprazole is solubilized in a minimum amount of PEG 300 (approximately 5 mL) or a minimum amount of propylene glycol (approximately 5 mL) by stirring and warming. 50 mg of polysorbate 80 is added, followed by the addition of 0.2 mL monoethanolamine. 2 mg of BHT, 10 mg of a sweetening agent and 10 mg of a flavoring agent are added to the mixture followed by the addition of a sufficient quantity of glycerol to bring the entire mixture to a volume of 10 mL. The amounts of the sweetening agent and flavoring agent can be adjusted to taste, in order to make a more palatable formulation. Various combinations of glycerol and PEG 300 can also be used to get the formulation to the desired consistency.

Example 4

500 mg of omeprazole is solubilized in a minimum amount of PEG 300 (approximately 5 mL) or a minimum amount of propylene glycol (approximately 5 mL) by stirring and warming. 50 mg of polysorbate 80 is added, followed by the addition of 0.2 mL monoethanolamine. 2 mg of BHT, 10 mg of a sweetening agent and 10 mg of a flavoring agent are added to the mixture followed by the addition of a sufficient quantity of sorbitol to bring the entire mixture to a volume of 10 mL. The amounts of the sweetening agent and flavoring agent can be adjusted to taste, in order to make a more palatable formulation. Various combinations of sorbitol and PEG 300 can also be used to get the formulation to the desired consistency.

Example 5

500 mg of omeprazole sodium salt is added to 5 mL PEG 300 or 5 mL of propylene glycol and the mixture is stirred. 2 mg of BHT, 10 mg of a sweetening agent, 50 mg phosphate buffer, and 10 mg of a flavoring agent are added to the mixture followed by the addition of a sufficient quantity of glycerol to bring the entire mixture to a volume of 10 mL. The amounts of the sweetening agent and flavoring agent can be adjusted to taste, in order to make a more palatable formulation. Various combinations of glycerol and PEG 300 can also be used to get the formulation to the desired consistency.

Example 6

500 mg of omeprazole sodium salt is added to 5 mL PEG 300 or 5 mL of propylene glycol and the mixture is stirred. 2 mg of BHT, 10 mg of a sweetening agent, 50 mg phosphate buffer, and 10 mg of a flavoring agent are added to the mixture followed by the addition of a sufficient quantity of sorbitol to bring the entire mixture to a volume of 10 mL. The amounts of the sweetening agent and flavoring agent can be adjusted to taste, in order to make a more palatable formulation. Various combinations of sorbitol and PEG 300 can also be used to get the formulation to the desired consistency.

Example 7

500 mg of omeprazole sodium salt is solubilized in a minimum amount of PEG 300 (approximately 5 mL) or a minimum amount of propylene glycol (approximately 5 mL) by stirring and warming. 50 mg of polysorbate 80, 2 mg of BHT, 10 mg of a sweetening agent, 50 mg phosphate buffer, and 10 mg of a flavoring agent are added to the mixture followed by the addition of a sufficient quantity of glycerol to bring the entire mixture to a volume of 10 mL. The amounts of the sweetening agent and flavoring agent can be adjusted to taste, in order to make a more palatable formulation. Various combinations of glycerol and PEG 300 can also be used to get the formulation to the desired consistency.

Example 8

500 mg of omeprazole sodium salt is solubilized in a minimum amount of PEG 300 (approximately 5 mL) or a minimum amount of propylene glycol (approximately 5 mL) by stirring and warming. 50 mg of polysorbate 80, 2 mg of BHT, 10 mg of a sweetening agent, 50 mg phosphate buffer, and 10 mg of a flavoring agent are added to the mixture followed by the addition of a sufficient quantity of sorbitol to bring the entire mixture to a volume of 10 mL. The amounts of the sweetening agent and flavoring agent can be adjusted to taste, in order to make a more palatable formulation. Various combinations of sorbitol and PEG 300 can also be used to get the formulation to the desired consistency.

Example 9

Figure 1:
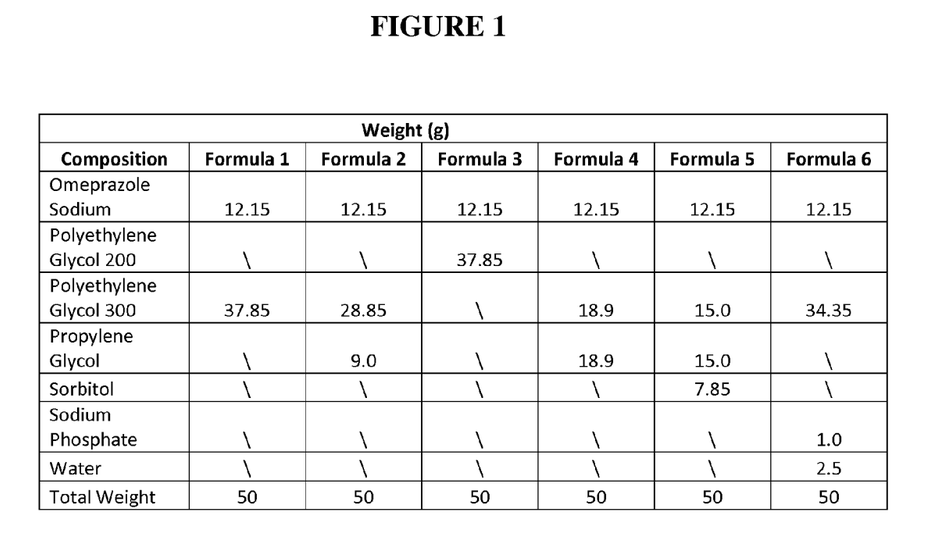
FIG. 1 is an exemplary table of exemplary compositions.

Further compositions are represented in FIG. 1. FIG. 1 is an exemplary table of exemplary compositions. As can be seen in FIG. 1, different compositions containing varying amounts of Omeprazole sodium, Polyethylene Glycol 200, Polyethylene Glycol 300, Propylene Glycol, Sorbitol, Sodium phosphate and water have varying effects on viscosity of the formulation. Viscosity, measured in centipoise (cPs), can be controlled by controlling the specific amounts of solubilizing agents, basifying agents and water. Not all elements which will be used in a final product were examined during these formations of exemplary compositions. Elements which were not examined during the formations of these exemplary compositions includes sweetening agents, flavoring agents, antioxidants, antimicrobial agents, solubility enhancers and other viscosity modifiers.

To form the compositions shown in FIG. 1, Omeprazole sodium was added in divided portions to combinations of Polyethylene Glycol 200, Polyethylene Glycol 300, Propylene Glycol, Sorbitol, Sodium phosphate and water until the Omeprazole sodium was substantially all dissolved. As an example, to form each of the compositions in FIG. 1, the amount of each component other than Omeprazole sodium was added to a vessel. For exemplary purposes, to form composition Formula 6, 34.35 grams of Polyethylene Glycol 300, 1.0 grams of sodium phosphate and 2.5 grams of water were added to a vessel. 12.15 grams of Omeprazole Sodium was then mixed in as further described below.

To increase the solubility of the Omeprazole sodium, the temperature of the mixture of the combinations of Polyethylene Glycol 200, Polyethylene Glycol 300, Propylene Glycol, Sorbitol, Sodium phosphate and water, as shown in FIG. 1, may be increased to about 28° C. to about 34° C. This increase in temperature decreases process time and results in an increased solubility of the Omeprazole sodium. After the full amount of Omeprazole sodium was added to the compositions of the combinations of Polyethylene Glycol 200, Polyethylene Glycol 300, Propylene Glycol, Sorbitol, Sodium phosphate and water as shown in FIG. 1, the resulting solution was cooled to room temperature followed by packaging into an amber glass container and fitting with a Teflon® lined cap.

The viscosity and stability of the formulas were measured over time. A portion of the containers containing each of the Formulas of FIG. 1 were stored at room temperature and ambient conditions while another portion of the containers containing each of the Formulas of FIG. 1 were stored at an "accelerated" test condition of 40° C. and 75% Relative Humidity to represent a non-ideal storage of the formula over time.

Figure 2:
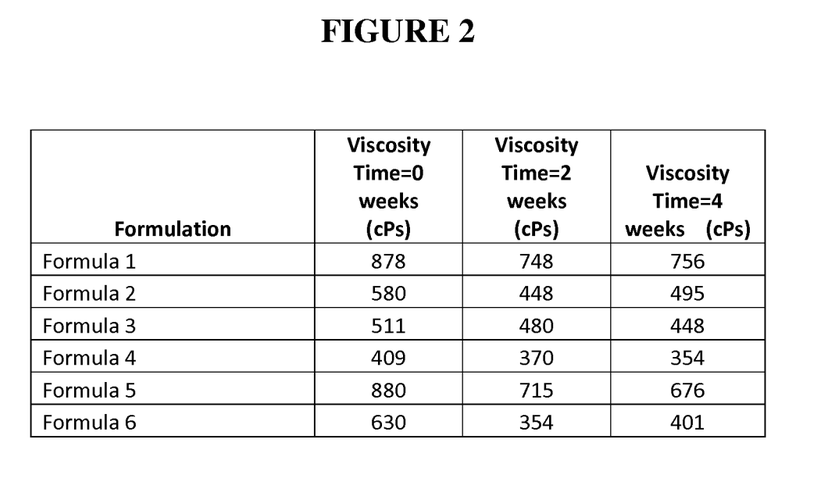
FIG. 2 is an exemplary table showing the measured viscosities for samples of each formula.

Samples of each of the Formulas of FIG. 1 were tested with a Brookfield viscometer using a cone and plate attachment for viscosity at room temperature. FIG. 2 represents measured viscosities for samples of each formula, stored at accelerated test condition of 40° C. and 75% Relative Humidity, at time zero, at two weeks and at four weeks after being placed and sealed in the storage containers. The samples in FIG. 2 were cooled to room temperature from 40° C. to measure viscosity. No change in microbial content was observed in the samples over time.

Figure 3:
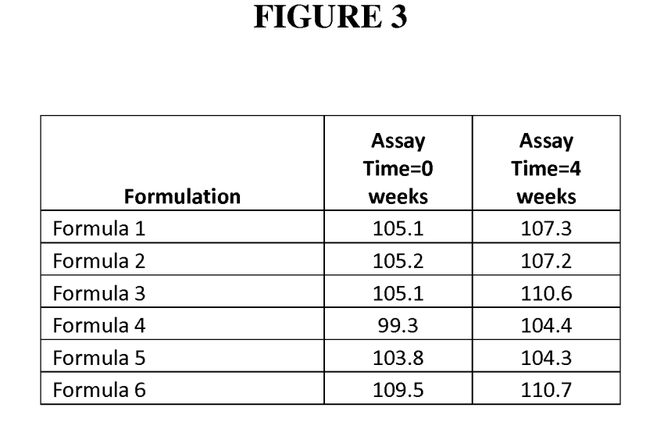
FIG. 3 is an exemplary table representing levels of active ingredient measured by assay and levels of impurities for samples of each formula.
Figure 4:
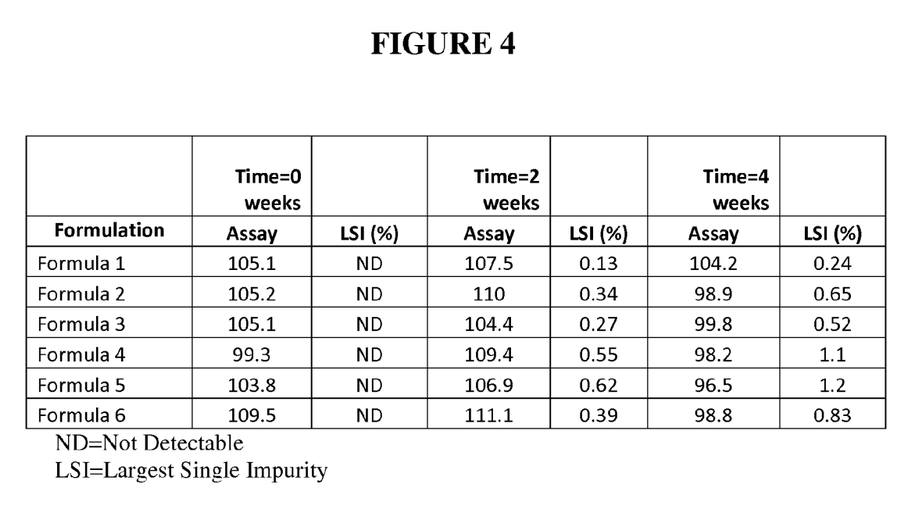
FIG. 4 is an exemplary table representing levels of active ingredient measured by assay and levels of impurities for samples of each formula, stored at accelerated test condition of 40° C. and 75% Relative Humidity.

Samples of each of the Formulas of FIG. 1 were tested using the current USP monograph method for assay, impurity and dissolution. FIG. 3 represents levels of active ingredient measured by assay and levels of impurities for samples of each formula, stored at ambient conditions, at time zero and at four weeks after being placed and sealed in the storage containers. The level of active ingredient remained stable over the four week testing period. No measurable impurities were detected in the samples represented in FIG. 3 over the time period. FIG. 4 represents levels of active ingredient measured by assay and levels of impurities for samples of each formula, stored at accelerated test condition of 40° C. and 75% Relative Humidity, at time zero, at two weeks and at four weeks after being placed and sealed in the storage containers. The level of active ingredient decreased slightly from time zero to week four. The largest single impurity increased slightly between zero weeks and four weeks.

Example 10

Figure 5:
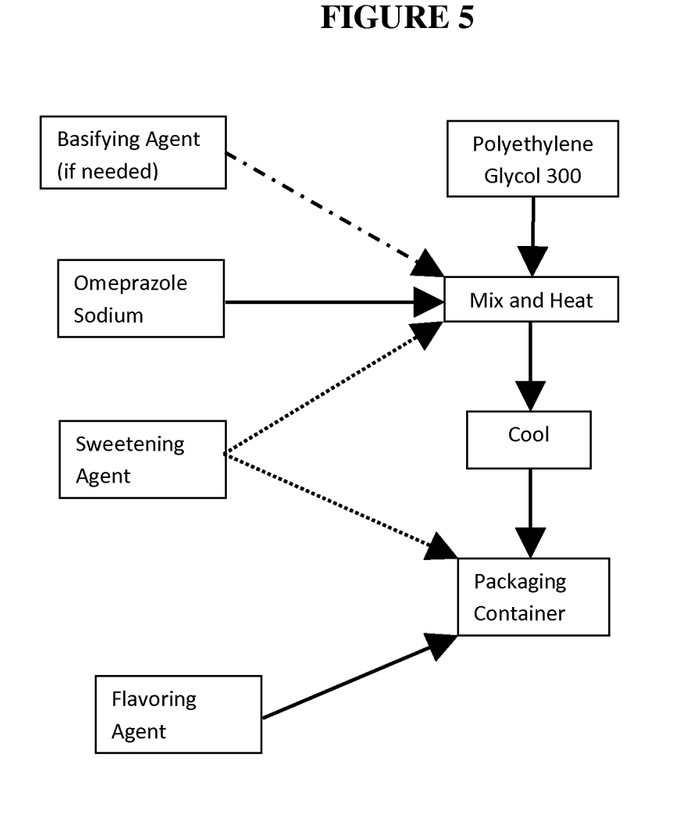
FIG. 5 is an exemplary flow chart of a method of making an omeprazole formulation.

One exemplary method of making an omeprazole formulation is described below and shown in FIG. 5. For exemplary purposes, making of the composition F-1, as shown in FIG. 1, is described. First, 12.15 grams of omeprazole sodium is weighed out separately from 37.85 grams of Polyethylene Glycol 300. Next the 37.85 grams of Polyethylene Glycol 300 is transferred to a suitable vessel and warmed to about 30° C. Then, a portion of the omeprazole sodium is gradually added to the vessel while the solution is being stirred at a medium high rate of stirring. At this step of warming and mixing, a basifying agent may be added if called for by the particular formulation. Also a sweetening agent may be added at this point or added at a later time prior to packaging. The solution is continually stirred until the solution is substantially clear. Portions of the remaining omeprazole sodium are added, each time the solution being continually stirred until the solution is substantially clear. After all omeprazole sodium has been added, the solution is cooled overnight to room temperature, transferred to a suitable container and sealed within the suitable container. A flavoring agent may be added prior to sealing within the suitable container.

Example 11

One exemplary embodiment of an omeprazole formulation was administered to three horses over a course of 2 weeks. The omeprazole formulation administered in this example was Formula I as shown and described in FIG. 1 and example 9 above. Each of the three horses was administered a dose of 20 mL of the omeprazole formulation, which included 2.28 grams of omeprazole per 10 mL of formula, once a day, each day for two weeks. The results of the administrations are described more fully below as they pertained to each individual horse.

Horse A was an 8 year old gelding Thoroughbred in active training and competition. At time zero, just prior to administration of the omeprazole formulation, he was suffering from grade 2+ to 3 (scale was 0 to 4, 0 indicating no ulceration and 4 indicating severe ulceration) ulcers within the squamous epithelium. After 2 weeks of treatment with the omeprazole formulation of the present invention, an endoscope was used to view the gastric lining of Horse A. Upon viewing the gastric lining, it could be seen that the ulcers had completely subsided to Grade 0 and the gastric mucosa was normal.

Horse B was a 13 year old gelding in active training and competition. At time zero, just prior to administration of the omeprazole formulation, he was suffering from a thickened, corrugated appearance of the gastric mucosa in the squamous portion with grade 2+ to 3 ulcers. After 2 weeks of treatment with the omeprazole formulation of the present invention, an endoscope was used to view the gastric lining of Horse B. Upon viewing the gastric lining, it could be seen that the ulcers had subsided to Grade 0-1 with a minimal thickening of the gastric mucosa along the margo plicatus.

Horse C was an 8 year old filly Thoroughbred in active training and competition. At time zero, just prior to administration of the omeprazole formulation, she was suffering from 2+ to 3 ulcers within the squamous mucosa. After 2 weeks of treatment with the omeprazole formulation of the present invention, an endoscope was used to view the gastric lining of Horse C. Upon viewing the gastric lining, it could be seen that the ulcers had completely subsided to Grade 0 with both the squamous and glandular portions being normal in appearance, there was no thickening along the margo plicatus and only minor fluid was found in the stomach.

What is claimed is:

1. A stable, palatable pharmaceutical syrup formulation for oral administration comprising:
    Omeprazole;
    a solubilizing agent;
    a basifying agent;
    a sweetening agent;
    a flavoring agent; and
    an antioxidant, wherein the syrup formulation has a viscosity of about 600 cPs at about 22° and the syrup formulation does not include a corticosteroid.

2. The pharmaceutical syrup formulation of claim 1, further comprising an antimicrobial agent selected from the group consisting of benzoic acid and sodium benzoate.

3. The pharmaceutical syrup formulation of claim 1, further comprising a solubility enhancer selected from the group consisting of cyclodextrins, Polysorbate 80 and Kollidon 17.

4. The pharmaceutical syrup formulation of claim 1, further comprising viscosity modifier selected from the group consisting of a cellulose source and xantham gum.

5. The pharmaceutical syrup formulation of claim 4, wherein the cellulose source is selected from the group consisting of hydroxyproxymethyl cellulose and hydroxypropyl methylcellulose.

6. The pharmaceutical syrup formulation of claim 1, wherein the solubilizing agent is selected from the group consisting of polyethylene glycol 200, polyethylene glycol 300, polyethylene glycol 400, propylene glycol, glycerol, sorbitol, dimethylisosorbide, and combinations thereof.

7. The pharmaceutical syrup formulation of claim 1, wherein the basifying agent is selected from the group consisting of monoethanolamine, diethanolamine, triethanolamine, and potassium hydroxide.

8. The pharmaceutical syrup formulation of claim 1, wherein the basifying agent comprises a combination of basifying agents, the basifying agents being selected from the group consisting of monoethanolamine, diethanolamine, triethanolamine, and potassium hydroxide.

9. The pharmaceutical syrup formulation of claim 1, wherein the sweetening agent is selected from the group consisting of stevia, sucralose, saccharin and aspartame.

10. The pharmaceutical syrup formulation of claim 1, wherein the flavoring agent is selected from the group consisting of apple and rosemary.

11. The pharmaceutical syrup formulation of claim 1, wherein the antioxidant is selected from the group consisting of BHA, BHT and propyl gallate.

12. The pharmaceutical syrup formulation of claim 1, wherein the formulation is orally administered for veterinary and human use.

13. A stable, palatable pharmaceutical syrup formulation for oral administration comprising:
    an omeprazole salt;
    a solubilizing agent;
    a buffer;
    a sweetening agent;
    a flavoring agent; and
    an antioxidant, wherein the syrup formulation has a viscosity of about 600 cPs at about 22° and the syrup formulation does not include a corticosteroid.

14. The pharmaceutical syrup formulation of claim 13, further comprising an antimicrobial agent selected from the group consisting of benzoic acid and sodium benzoate.

15. The pharmaceutical syrup formulation of claim 13, further comprising a solubility enhancer selected from the group consisting of cyclodextrins, Polysorbate 80 and Kollidon 17.

16. The pharmaceutical syrup formulation of claim 13, further comprising viscosity modifier selected from the group consisting of a cellulose source and xanthan gum.

17. The pharmaceutical syrup formulation of claim 16, wherein the cellulose source is selected from the group consisting of hydroxyproxymethyl cellulose and hydroxypropyl methylcellulose.

18. The pharmaceutical syrup formulation of claim 13, wherein the solubilizing agent is selected from the group consisting of polyethylene glycol 200, polyethylene glycol 300, polyethylene glycol 400, propylene glycol, dimethylisosorbide, glycerol, sorbitol and combinations thereof.

19. The pharmaceutical syrup formulation of claim 13, wherein the sweetening agent is selected from the group consisting of stevia, sucralose, saccharin and aspartame.

20. The pharmaceutical syrup formulation of claim 13, wherein the flavoring agent is selected from the group consisting of apple and rosemary.

21. The pharmaceutical syrup formulation of claim 13, wherein the antioxidant is selected from the group consisting of BHA, BHT and propyl gallate.

22. The pharmaceutical syrup formulation of claim 13, wherein the buffer selected is a phosphate buffer.

23. The pharmaceutical syrup formulation of claim 22, wherein the phosphate buffer provides a pH above 8 in the gastric environment.

24. The pharmaceutical syrup formulation of claim 13, wherein the formulation is orally administered for veterinary and human use.

25. The pharmaceutical syrup formulation of claim 13, wherein the omeprazole salt is selected from the group consisting of sodium, lithium, potassium, calcium and magnesium salts, and combinations thereof.

26. A kit comprising:
a concentrated amount of the pharmaceutical syrup formulation of claim 1 or the pharmaceutical syrup formulation of claim 12;
a vessel; and
a syringe.

27. The kit of claim 26 further comprising a dilutant.

28. The kit of claim 27, wherein the dilutant is water.

29. A stable, palatable pharmaceutical syrup formulation for oral administration comprising:
omeprazole;
a solubilizing agent;
two or more basifying agents;
a sweetening agent;
a flavoring agent; and
an antioxidant, wherein the syrup formulation has a viscosity of about 600 cPs at about 22° and the syrup formulation does not include a corticosteroid.

30. The pharmaceutical syrup formulation of claim 29, further comprising an antimicrobial agent selected from the group consisting of benzoic acid and sodium benzoate.

31. The pharmaceutical syrup formulation of claim 29, further comprising a solubility enhancer selected from the group consisting of cyclodextrins, Polysorbate 80 and Kollidon 17.

32. The pharmaceutical syrup formulation of claim 29, further comprising viscosity modifier selected from the group consisting of a cellulose source and xanthan gum.

33. The pharmaceutical syrup formulation of claim 32, wherein the cellulose source is selected from the group consisting of hydroxyproxymethyl cellulose and hydroxypropyl methylcellulose.

34. The pharmaceutical syrup formulation of claim 29, wherein the solubilizing agent is selected from the group consisting of polyethylene glycol 200, polyethylene glycol 300, polyethylene glycol 400, propylene glycol, glycerol, sorbitol, dimethylisosorbide, and combinations thereof.

35. The pharmaceutical syrup formulation of claim 29, wherein the two or more basifying agents are selected from the group consisting of monoethanolamine, diethanolamine, triethanolamine, potassium hydroxide and combinations thereof.

36. The pharmaceutical syrup formulation of claim 29, wherein the basifying agent comprises a combination of basifying agents, the basifying agents being selected from the group consisting of monoethanolamine, diethanolamine, triethanolamine, and potassium hydroxide.

37. The pharmaceutical syrup formulation of claim 29, wherein the sweetening agent is selected from the group consisting of stevia, sucralose, saccharin and aspartame.

38. The pharmaceutical syrup formulation of claim 29, wherein the flavoring agent is selected from the group consisting of apple and rosemary.

39. The pharmaceutical syrup formulation of claim 29, wherein the antioxidant is selected from the group consisting of BHA, BHT and propyl gallate.

40. The pharmaceutical syrup formulation of claim 29, wherein the formulation is orally administered for veterinary and human use.

41. A method of making a stable, palatable pharmaceutical syrup formulation for oral administration comprising the steps of:
adding an amount of solubilizing agent, sweetening agent and flavoring agent into a vessel;
warming the amount of solubilizing agent, sweetening agent and flavoring agent in the vessel;
adding an amount of omeprazole to the warmed amount of solubilizing agent, sweetening agent and flavoring agent in the vessel;
stirring the contents of the vessel until the contents are substantially clear;
adding the remaining amount of omeprazole to the vessel;
stirring the contents of the vessel until the contents are substantially clear; and
transferring the contents of the vessel to a suitable container; wherein the syrup formulation has a viscosity of about 600 cPs at about 22° and the syrup formulation does not include a corticosteroid.

42. The method of claim 41, wherein the vessel is warmed to about 30° C.

43. The method of claim 41, wherein the omeprazole is an omeprazole salt selected from the group consisting of sodium, lithium, potassium, calcium and magnesium salts, and combinations thereof.

44. The method of claim 41, further comprising the addition of a basifying agent to the vessel in the first step.

45. The pharmaceutical syrup formulation of claim 1, wherein the syrup formulation maintains levels of omeprazole that are about the same after four weeks of storage at room temperature.

46. The pharmaceutical syrup formulation of claim 29, wherein the syrup formulation maintains levels of omeprazole that are about the same after four weeks of storage at room temperature.

47. The pharmaceutical syrup formulation of claim 1, wherein the syrup formulation maintains levels of omeprazole within about 10% after four weeks of storage at 40° C. and 75% relative humidity.

48. The pharmaceutical syrup formulation of claim 29, wherein the syrup formulation maintains levels of omeprazole within about 10% after four weeks of storage at 40° C. and 75% relative humidity.

49. The pharmaceutical syrup formulation of claim 1, wherein the largest single impurity in the syrup formulation is about 0.39% of the syrup formulation after four weeks of storage at 40° C. and 75% relative humidity.

50. The pharmaceutical syrup formulation of claim 29, wherein the largest single impurity in the syrup formulation is about 0.39% of the syrup formulation after four weeks of storage at 40° C. and 75% relative humidity.

51. The pharmaceutical syrup formulation of claim 1, wherein the syrup formulation has a viscosity of about 400 cPs at about 22° C. after four weeks of storage at 40° C. and 75% relative humidity.

52. The pharmaceutical syrup formulation of claim 29, wherein the syrup formulation has a viscosity of about 400 cPs at about 22° C. after four weeks of storage at 40° C. and 75% relative humidity.

* * * * *